United States Patent
Aiache et al.

(12)

(10) Patent No.: US 6,187,323 B1
(45) Date of Patent: Feb. 13, 2001

(54) STABLE GEL MIXTURE IN THE FORM OF A MIXTURE OF OLEOGEL AND AQUEOUS GEL, PROCESS FOR ITS PREPARATION, PHARMACEUTICAL AND COSMETIC COMPOSITIONS COMPRISING IT, AND USE OF THE PHARMACEUTICAL COMPOSITIONS

(75) Inventors: Jean-Marc Aiache; Pascale Gauthier, both of Clermont-Ferrand Cedex (FR)

(73) Assignee: Zentrx, Inc., Encinitas, CA (US)

( * ) Notice: Under 35 U.S.C. 154(b), the term of this patent shall be extended for 0 days.

(21) Appl. No.: 09/204,089

(22) Filed: Dec. 3, 1998

(30) Foreign Application Priority Data

Jun. 3, 1998 (FR) .................................................. 98 06958

(51) Int. Cl.$^7$ .............................. A61K 6/00; A61K 7/00; A61K 31/74; A61K 9/70; A61F 13/00
(52) U.S. Cl. ......................... 424/401; 424/443; 424/447; 424/449; 424/78.02
(58) Field of Search ................................ 424/401, 78.02, 424/443, 447, 449; 514/944, 969

(56) References Cited

FOREIGN PATENT DOCUMENTS

| 0 793 966 | 9/1997 | (EP) . |
| 0793966 * | 9/1997 | (EP) . |
| 93/20799 | 10/1993 | (WO) . |

OTHER PUBLICATIONS

Database Search, XP–002093985, "New gelification method for vegetable oils I: cosmetic application", Int. J. Cosmet. Sci., vol. 14, No. 5, pp. 228–234, (1992).
Database Search, XP–002093986, "New gelification for vegetal oils", Bull. Tech./Gattefosse Rep., vol. 84, pp. 71–76, (1991).
Database Search, XP–002093987, "Novel glyceride gels II. Viscosity characteristics", Int. J. Cosmet. Sci., vol. 18, No. 5, pp. 229–235, (Oct. 1996).
Aiache et al. New Gelification Method for Vegetable Oils I: Cosmetic Application, International Journal of Cosmetic Science 14;228–234, 1992*

* cited by examiner

Primary Examiner—Thurman K. Page
Assistant Examiner—Todd D. Ware

(57) ABSTRACT

The present invention relates to a stable gel mixture, having a substantially uniform appearance, which stable gel mixture comprises at least one oleogel and of at least one aqueous gel, the oleogel comprising at least one oily agent gelled with at least one cellulose polymer. The present invention also relates to a pharmaceutical composition comprising this gel, to the use of this pharmaceutical composition as a reservoir for active ingredients in a transdermal release system, as well as to a cosmetic composition comprising this gel. This gel has remarkable stability and a fresh and pleasant feel.

18 Claims, No Drawings

STABLE GEL MIXTURE IN THE FORM OF A MIXTURE OF OLEOGEL AND AQUEOUS GEL, PROCESS FOR ITS PREPARATION, PHARMACEUTICAL AND COSMETIC COMPOSITIONS COMPRISING IT, AND USE OF THE PHARMACEUTICAL COMPOSITIONS

The present invention relates to a stable gel mixture in the form of a mixture of oleogel and aqueous gel, to a process for preparing this stable gel mixture, to a pharmaceutical composition comprising this stable gel mixture, to the use of this composition as a reservoir of active ingredients in a transdermal release system and, lastly, to a cosmetic composition comprising this stable gel mixture.

It is known to prepare oleogels, in particular by gelling a synthetic, semisynthetic or natural oil, in order to combine the relatively solid consistency of a gel with the total transparency of an oil.

However, oleogels have the drawback of feeling greasy and unpleasant, on account of the presence of the oily compound. This unpleasant feel very often discourages users, in particular in the case of dermatological and cosmetic applications.

It is thus desirable, for example, to be able to give a bodycare oil a relatively solid consistency but with a non-greasy, fresh and pleasant feel, while at the same time keeping the original appearance of the oil. The reason for this is that oils are difficult for users to control because of their excessive fluidity. In particular, the use of bath oils makes the bath slippery and accounts for approximately 3% of the serious accidents in bathrooms.

It has now been found, entirely surprisingly and unexpectedly, that the mixture of a certain type of oleogel with an aqueous gel makes it possible to obtain a gel of substantially uniform appearance, which is remarkably stable and has a fresh and pleasant feel.

Thus the subject of the present invention is a stable gel, substantially uniform appearance, that comprises a mixture, of at least one oleogel and at least one aqueous gel, the oleogel comprising at least one oily agent gelled with at least one cellulose polymer.

According to the invention, the expression "mixture of substantially uniform appearance" is understood to mean an intimate mixture, and not an emulsion, of the oleo and aqueous gels, that is, a uniform dispersion of one in the other, such that, when inspected visually, only a single gel can be distinguished, and when applied to the skin, no separation of the two aqueous gel and oleogel phases is detected.

The intimate nature of the mixture of the two types of gel can be controlled, for example, by introducing a dye substance into the oily or aqueous gel, before forming the mixture, in order to visually observe the uniform dispersion of this dye substance after forming the mixture, even though the dye is present in only one of the two types of gel—oily or aqueous—of the stable gel mixture formed.

According to the invention, the term "stable gel" is understood to mean the stable mixture of oily and aqueous gels of a uniform appearance without any demixing on storage.

In particular, the cellulose polymer is chosen from ethylcellulose, non-sodium containing carboxymethylcellulose, and mixtures thereof.

The oily agent is chosen in particular from mono-, di- and triglycerides of synthetic, semisynthetic and natural origin, and mixtures thereof.

As synthetic mono-, di- or triglycerides, reference is made in particular to Miglyol 810 and 812, as sold by the company Dynamit Nobel.

As semisynthetic mono-, di- or triglycerides, reference is made in particular to propylene glycol isostearate, such as the product sold under the name "hydrophilol isostéarique" by the company Gatefossé, and the polyglycolysed glyceride "Labrafil® M 1944 Cs" as sold by the company Gatefossé.

Labrafil® M 1944 CS is a mixture of polyoxyethylenated oleic glycerides obtained by alcoholysis of natural plant oil (French Pharmacopoeia, 8th edition). It is an oily liquid whose properties are presented in Table 1 below.

Lastly, as mono-, di- or triglycerides of natural origin, reference is made in particular to oils of plant origin, such as sweet almond oil, argan oil and palm oil.

According to a preferred embodiment of the present invention, the cellulose polymer is ethyl-cellulose, present in a proportion of between about 1 and about 10% by weight, and the oily agent comprises Labrafil® M 1944 CS, present in a proportion of between about 5 and about 90% by weight, relative to the total weight of the oleogel, the ratio of the weight of oleogel to the weight of aqueous gel being between about 10:90 and about 90:10.

Preferably, the oily agent further comprises propylene glycol isostearate, in a proportion of between about 5 and about 90% by weight, relative to the total weight of the oleogel.

TABLE 1

| Chemical name | Polyglycolysed oleic glyceride (cores) |
|---|---|
| Trade name | Labrafil M 1944 CS |
| Drop point ° C. | Liq. |
| Saponification number | 1451175 |
| Acid number | <2 |
| Iodine number | 60/90 |
| Oral acute toxicity/rat | OLD >20 ml/kg |
| LOP | 0 |
| HLB | 314 |

The aqueous gel present in the stable gel mixture according to the invention comprises at least one gelling agent preferably chosen from carbomers, poloxamers, sodium carboxymethylcellulose and mixtures of the latter, the gelling agent being present in a proportion of between about 0.1 and about 10% by weight, relative to the total weight of the aqueous gel, the ratio of the weight of oleogel to the weight of aqueous gel formed being between about 10:90 and about 90:10.

More particularly, the gelling agent for the aqueous gel is the carbomer Carbopol 974, present in a proportion of between about 0.1 and about 5% by weight, relative to the total weight of the aqueous gel.

Needless to say, the oleogel and the aqueous gel can, respectively, further comprise standard ingredients for a gel, such as texture agents, antioxidants such as butylated hydroxyanisole (BHA) or butylated hydroxytoluene (BHT), dyes or fragrances.

The subject of the present invention is also a process for the preparation of the stable gel mixture as defined above, this process being characterized in that it comprises the steps consisting of:

a) separately forming the oleogel and the aqueous gel, the viscosity of the oleogel formed being adjusted, where necessary by heating preferably to temperature of not more than 50° C., to a value of between about 20 and about 40 Pa.s, and the viscosity of the aqueous gel formed being adjusted, where necessary by heating preferably to a temperature of not more than 50° C.; to a value of between about 10 and about 30 Pa.s, and b) incorporating the oleogel into the aqueous gel or, vice versa, with non-shear stirring, until a mixture of substantially uniform appearance, as already defined above, is obtained.

The respective formations of the oleogel and of the aqueous gel in step a) are carried out according to operating conditions known to those skilled in the art. Reference will be made in particular to the examples below.

According to the invention, the expression "non-shear stirring", for the incorporation of the oleogel into the aqueous gel, or vice versa, in accordance with step b) of the present process, is understood to refer in particular to a non-destructive stirring of the respective gels of oily and aqueous types, for the formation of a mixture of substantially uniform appearance.

Preferably, a planetary mixer is used, such as those sold by the companies Hobart or Kenwood, set to a maximum speed of about 5 revolutions/minute for about 10 to 20 minutes.

In general, the settings for the other operating conditions in order to carry out the present process are within the scope of those skilled in the art.

The subject of the present invention is also a stable pharmaceutical composition, which can be administered topically, orally or parenterally, characterized in that it comprises a stable gel mixture as defined above, and at least one of the oleogel or the aqueous gel components further comprises at least one active ingredient(s).

Needless to say, depending on the route of administration envisaged, the viscosity of the composition is adjusted to an appropriate value, in particular by adapting the proportions of gelling agents in the aqueous gel phase or in the oleogel phase, or both.

In particular, given its biodegradable nature, the composition according to the invention can be administered as an injection. It is thus possible to inject allergens or vaccines which are known to be effective only under special administration conditions e.g. in a special solvent that improve antibody formation, such as the Incomplete Freund's Adjuvant (a mixture of an internal aqueous phase dispersed in an external oily phase consisting of mannide monooleate (Arlacel A)). The Incomplete Freund's Adjuvant, however, causes serious inflammatory side effects at the site injection, because it causes a chronic inflammatory response that may be severe and painful depending on the site as well as the quantity and quality of adjuvant injected. The inflammatory response may result in formation of chronic granulomas, sterile abscesses, and/or ulcerating tissue necrosis. In contrast, the oleogel can have the same beneficial properties in aiding the immune response and stimulating antibody formation, but do not have such inflammatory side effects.

Whatever the route of administration envisaged, the active ingredient(s) of the pharmaceutical composition according to the invention can be any pharmaceutically active ingredient(s), such as the above mentioned allergens and vaccines; substances such as hormones which require sustained release while at the same time maintaining good tolerance; or alternatively dermatologically active ingredient(s).

In addition, the pharmaceutical composition according to the invention can advantageously comprise at least one active ingredient(s) in the oleogel and at least one active ingredient(s) in the aqueous gel, it being possible for at least one active ingredient(s) in the oleogel to be incompatible with at least one active ingredient(s) in the aqueous gel.

According to the invention, the expression "incompatible active ingredient(s)" is understood to refer to active ingredient(s) which are capable of reacting together in a chemically or therapeutically undesirable manner. Insofar as the incompatible active ingredient(s) are mainly soluble, respectively, in the oleogel or the aqueous gel of the composition according to the invention, it has been observed that any contact and thus any adverse reaction between the active ingredient(s) before their administration can thus be avoided.

In particular, the pharmaceutical composition according to the invention can comprise β-oestradiol in the oleogel, in a proportion of between 0.1 and about 5% by weight, relative to the total weight of the oleogel, and progesterone in the aqueous gel, in a proportion of between about 1 and about 6% by weight, relative to the total weight of the aqueous gel, the ratio of the weight of oleogel to the weight of aqueous gel being between about 10:90 and about 90:10 and preferably between 30:70 and 70:30.

In certain cases, in particular for the purpose of a topical administration, the pharmaceutical composition according to the invention can comprise the same active ingredient(s) in the oleogel and the aqueous gel.

This is because, in the case of a topical administration, the profile for release of the active ingredient(s) into the skin has been found to be considerably better than that obtained with a composition based on only one type of gel, oily or aqueous, for a given volume of composition applied and a given concentration of active ingredient(s) relative to the total weight of the composition.

This result is particularly advantageous when such a composition is used as an active ingredient(s) reservoir in a transdermal release system as mentioned below. The reason for this is that, on the skin, the amount of active ingredient(s) dissolved in the aqueous gel phase is rapidly taken up by the epidermal layers, which allows the percutaneous passage to start quickly. The amount of active ingredient(s) dissolved in the oleogel phase must firstly, as a function of its oil/water partition coefficient, pass into the aqueous gel phase in order to pass into the epidermal layers. Thus the fraction in the oleogel will be released with a greater delay, after the active ingredient(s) dissolved in the aqueous gel phase has been released.

In particular, the pharmaceutical composition according to the invention can advantageously comprise testosterone in the oleogel and the aqueous gel, the proportion of testosterone in the oleogel being between 0.1 and 6% by weight, relative to the total weight of the oleogel, and the proportion of testosterone in the aqueous gel being between about 1 and 10% by weight, relative to the total weight of the aqueous gel, and the ratio of the weight of the oleogel to the weight of the aqueous gel being between about 10:90 and about 90:10 and preferably between 30:70 and 70:30.

It has also been observed, surprisingly, that the stable gel mixture according to the invention is particularly suitable for containing a sulphur-containing active ingredient(s), whose characteristic unpleasant odor proves to be advantageously confined in the stable gel mixture and thus cannot be perceived by the user.

Thus, the active ingredient(s) of the pharmaceutical composition according to the invention can be a sulphur-containing active ingredient(s), contained in the aqueous or oleogel.

According to the present invention, the expression sulphur-containing active ingredient(s) is understood to refer in particular to those whose bonding with the sulphur atom is labile, such as the sulphur-containing amino acids and spironolactone.

In particular, the sulphur-containing active ingredient(s) is spironolactone, present in the oleogel in a proportion of between about 0.5 and about 10% by weight, relative to the total weight of the oleogel, the ratio of the weight of the oleogel to the weight of the aqueous gel being between about 10:90 and about 90:10 and preferably between 40:60 and 60:40.

The composition according to the invention, as described above, can be prepared by simply adding the active ingredient(s) during the process for the preparation of the stable gel mixture as already described above. In particular, depending on the pharmaceutical composition envisaged, the active ingredient(s) can be added to the oleogel and/or to the aqueous gel before preparing the oleogel-aqueous gel mixture of substantially uniform appearance. This is the case, in particular, when at least two mutually incompatible active ingredient(s), as defined above, are used, each of the active ingredient(s) being added, one to the oleogel and the other to the aqueous gel. It is also possible to add the active ingredient(s) to the preformed stable gel mixture according to the invention, with stirring, the active ingredient(s) thus being distributed in both the oleogel and the aqueous gel.

Needless to say, a person skilled in the art will know to take into account the characteristics of the active ingredient(s) used, adapting the operating conditions of the process, in particular the temperature, so as possibly not to adversely affect the properties of the active ingredient(s).

The subject of the present invention is also the use of the pharmaceutical composition, as described above, as an active ingredient(s) reservoir in a transdermal release system.

Lastly, the subject of the present invention is also a stable cosmetic composition, characterized in that it comprises a stable gel mixture as defined above, at least one from among the oleogel and the aqueous gel comprising at least one cosmetically active ingredient.

The cosmetically active ingredient can be any ingredient which gives a cosmetic effect, i.e. an ingredient which, when placed in contact with the various external parts of the human body (epidermis, pilous and hair system, nails, lips and outer genital organs) or with the teeth or oral mucosae, by means of the composition, makes it possible, exclusively or mainly, to cleanse them, to fragrance them, to modify their appearance and/or to correct body odors and/or to protect them or keep them in good condition.

The cosmetically active ingredient can thus be, in particular, moisturizers, sunscreens, anti-free-radical agents or skin regenerators which are soluble in either the oleogel or the aqueous gel phases.

Advantageously, given the problems posed by body-care oils in cosmetics, such as bath oils, as explained at the start of the present description, the cosmetically active ingredient is advantageously chosen from body-care oils, and more particularly from bath oils such as palm oil, sesame oil or argan oil.

It will thus be understood in particular that the oily agent, as defined above, can advantageously constitute a cosmetically active ingredient in the meaning of the invention.

Depending on the type of cosmetically active ingredient used, a person skilled in the art will know how to determine its appropriate proportion by weight, relative to the total weight of the cosmetic composition according to the invention.

The present invention will now be illustrated with the aid of examples, which should not however, under any circumstances, be interpreted as limiting as regards the scope of the invention.

In the text hereinbelow, except where otherwise specified, the percentages indicated are percentages by weight.

EXAMPLE 1

Preparation of an ethylcellulose+Labrafil M 1944 CS+propylene glycol isostearate+Carbopol 974 gel 1.1 Preparation of the oleogel.

The ingredients below are introduced into a Rayneri-type heating mixer, for a mixing temperature of 140° C., the stirring being set at 30 revolutions/minute:

| Labrafil ® M 1944 CS | 82.5 |
|---|---|
| Propylene glycol isostearate | 8.5 |
| Hercules N 50 NF ethylcellulose | 6 |
| Sesame oil | 1 |
| Ethanol | 0.5 |
| BHA | 0.5 |
| BHT | 0.5 |
| Fragrance | 0.5 |
| | 100% |

The stirring and the temperature are maintained until a uniform oleogel is obtained. The stirring is then switched off and the mixture is left to cool to room temperature. The oleogel thus obtained has a viscosity of about 60 Pa.s at room temperature.

1.2 Preparation of the aqueous gel.

The following ingredients are introduced into another heating mixer, for a mixing temperature of 30° C., with stirring at 30 revolutions/minute:

| Carbopol 974 | 0.3 |
|---|---|
| Water:ethanol mixture (weight ratio 6:5) | 99.7 |
| | 100% |

The stirring and the temperature are maintained until a uniform aqueous gel is obtained. The stirring is then switched off and the aqueous gel is left to cool to room temperature.

1.3 Preparation of the stable gel mixture according to the invention.

The aqueous gel and then the oleogel which are prepared as described in sections 1.1 and 1.2 above are successively introduced into a planetary heating mixer sold by the company Kenwood, set at a speed of 5 revolutions/minute and at a heating temperature of 50° C., the weight ratio of the oleogel to the aqueous gel in the mixture thus formed being 10:90.

The stirring and the temperature are maintained until a gel in the form of a mixture of substantially uniform appearance is obtained. The stirring is then switched off and the mixture is left to cool to room temperature.

The stable gel mixture according to the invention thus prepared has, simultaneously, a thick consistency, a fresh and pleasant feel and surprising stability since no demixing between the oleogel and the aqueous gel was observed on storing the stable gel mixture for a period of more than five years.

Moreover, this stable gel mixture has very good in vitro adhesiveness, which is a parameter that indicates the adhesion of the stable gel mixture to the skin when it is applied thereto.

Measurement of the in vitro adhesiveness was carried out with a "TEC" texturometer as sold by the company ETIA.

The results obtained, in cycles, are as follows:

| | |
|---|---|
| In vitro adhesiveness (mJ) | 0.608 |
| force min (N) | −0.076 |
| Time (sec) | 15.8 |

On account of its excellent in vitro adhesiveness, the stable gel mixture thus obtained can advantageously be used, by incorporating a pharmaceutically active ingredient (s) therein, as a reservoir layer of a system for the transdermal release of the active ingredient(s).

EXAMPLE 2

Pharmaceutical composition comprising β-oestradiol and progesterone

The process is performed as in section 1.1 of Example 1, after which an amount of 1% by weight of β-oestradiol, relative to the total weight of the oleogel, is added to the formed oleogel, with stirring and at a temperature set at 50° C., until the β-oestradiol has been uniformly dispersed in the oleogel.

Separately, the process is performed as in section 1.2 of Example 1, after which an amount of 5% by weight of progesterone, relative to the total weight of the aqueous gel, is added to the formed aqueous gel, with stirring and at a temperature set at 50° C., until the progesterone has been uniformly dispersed in the aqueous gel.

The pharmaceutical composition according to the invention is then formed by incorporating the oleogel (containing the β-oestradiol) into the aqueous gel (containing the progesterone) as in section 1.3 of Example 1, the weight ratio of the oleogel to the aqueous gel being 10:90.

EXAMPLE 3

Pharmaceutical composition comprising testosterone

The process is performed as in Example 2, using 35 testosterone as active ingredient(s) instead of β-oestradiol and progesterone. To do this, a proportion of 5% by weight of testosterone, relative to the total weight of the oleogel, is introduced into the oleogel, and, separately, a proportion of 5% by weight of testosterone, relative to the total weight of the aqueous gel, is introduced into the aqueous gel. A weight ratio of oleogel to the aqueous gel of 90:10 is used.

The testosterone-based pharmaceutical composition thus prepared can advantageously be used as a testosterone-reservoir layer in the form of a gel in a transdermal release system.

EXAMPLE 4

Pharmaceutical composition comprising spironolactone

The process is performed as in section 1.1 of Example 1, after which an amount of 5% by weight of spironolactone, relative to the total weight of the oleogel, is added to the formed oleogel, with stirring and at a temperature set at 50° C., until the spironolactone has been uniformly dispersed in the oleogel.

Separately, the process is performed as in section 1.2 of Example 1 in order to form the aqueous gel.

The pharmaceutical composition according to the invention is thus prepared by incorporating the oleogel (containing the spironolactone) to the aqueous gel as in section 1.3 of Example 1, the weight ratio of the oleogel to the aqueous gel being 60:40.

The spironolactone-based pharmaceutical composition according to the invention thus obtained is, surprisingly, substantially free of the unpleasant odor characteristic of the presence of spironolactone, which represents an advantageous deciding factor for users, when compared with the known spironolactone-based pharmaceutical compositions.

What is claimed is:

1. A stable gel mixture, that has a substantially uniform appearance and that comprises at least one oleogel and at least one aqueous gel, the oleogel comprising at least one oily agent gelled with at least one cellulose polymer.

2. The stable gel mixture according to claim 1, wherein the cellulose polymer is an ethylcellulose, a non-sodium containing carboxymethylcellulose, or a mixture thereof.

3. The stable gel mixture according to claim 1, wherein the oily agent is a mono-, di- and triglycerides of synthetic, semisynthetic or natural origin, or a mixtures thereof.

4. The stable gel mixture according to claim 3, wherein the oily agent is selected from the group consisting of a synthetic di- or triglyceride; a propylene glycol isostearate; a mixture of polyoxyethylenated oleic glycerides and an oil of plant origin.

5. The stable gel mixture according to claim 1, wherein the cellulose polymer is an ethyl-cellulose, present in a proportion of between about 1% and about 10% by weight relative to the total weight of the oleogel; wherein the oily agent comprises a mixture of polyoxyethylenated oleic glycerides, present in a proportion of between about 5% and about 90% by weight, relative to the total weight of the oleogel; and wherein the ratio of the weight of oleogel to the weight of aqueous gel is between about 10:90 and about 90:10.

6. The stable gel mixture according to claim 5, wherein the oleogel further comprises propylene glycol isostearate, in a proportion of between about 5% and about 90% by weight, relative to the total weight of the oleogel.

7. The stable gel mixture according to claim 1, wherein the aqueous gel comprises at least one gelling agent selected from the group consisting of carbomers, poloxamers, sodium carboxymethylcellulose and mixtures thereof, wherein the gelling agent is present in a proportion of between about 0.1% and about 10% by weight, relative to the total weight of the aqueous gel, and wherein the ratio of the weight of oleogel to the weight of aqueous gel is between about 10:90 and about 90:10.

8. The stable gel mixture according to claim 7, wherein the gelling agent is a carbomer, present in a proportion of between about 0.1% and about 5% by weight, relative to the total weight of the aqueous gel.

9. A process for the preparation of the stable gel mixture according to claim 1, comprising the steps of:
   a) forming an oleogel, the viscosity of the oleogel formed being adjusted, where necessary by heating, to a value of between about 20 and about 40 Pa.s;
   b) forming an aqueous gel, the viscosity of the aqueous gel formed being adjusted, where necessary by heating, to a value of between about 10 and about 30 Pa.s; and
   c) incorporating the oleogel formed into the aqueous gel or vice versa, with non-shear stirring, until a stable gel mixture of substantially uniform appearance is obtained.

10. A stable pharmaceutical composition, which can be administered topically, orally or parenterally, comprising a stable gel mixture according to claim 1, and at least one pharmaceutically active ingredient in at least one of the oleogels or the aqueous gels.

11. The pharmaceutical composition according to claim 10, wherein the oleogel comprises at least a first active ingredient and the aqueous gel comprises at least a second active ingredient, wherein the first and second active ingredients are incompatible or compatible with each other.

12. The pharmaceutical composition according to claim 10, wherein the oleogel comprises β-oestradiol, in a proportion of between 0.1% and about 5% by weight, relative to the total weight of the oleogel; wherein the aqueous gel comprises progesterone, in a proportion of between about 1% and about 6% by weight, relative to the total weight of the aqueous gel; and wherein the ratio of the weight of oleogel to the weight of aqueous gel is between about 10:90 and about 90:10.

13. The pharmaceutical composition according to claim 10, wherein the oleogel comprises testosterone, in a proportion of between 0.1% and 6% by weight, relative to the total weight of the oleogel; wherein the aqueous gel comprises testosterone, in a proportion of between about 1% and about 10% by weight, relative to the total weight of the aqueous gel; and wherein the ratio of the weight of oleogel to the weight of aqueous gel is between about 10:90 and about 90:10.

14. The pharmaceutical composition according to claim 10, wherein the active ingredient is a sulphur-containing active ingredient.

15. The composition according to claim 14, wherein the sulphur-containing active ingredient is spironolactone present in the oleogel in a proportion of between about 0.5% and about 10% by weight, relative to the total weight of the oleogel, and wherein the ratio of the weight of oleogel to the weight of aqueous gel is between about 10:90 and about 90:10.

16. A method for preparing a transdermal releasing composition comprising adding at least one active ingredient to the pharmaceutical composition according to claim 10, wherein the pharmaceutical composition according to claim 10 serves as an active ingredient reservoir in a transdermal release system.

17. A stable cosmetic composition, comprising the stable gel mixture according to claim 1, wherein at least one of the oleogels or the aqueous gels comprise at least one cosmetically active ingredient.

18. The cosmetic composition according to claim 17, wherein the cosmetically active ingredient is a body-care oil.

* * * * *